(12) United States Patent
Groot et al.

(10) Patent No.: US 12,246,090 B2
(45) Date of Patent: Mar. 11, 2025

(54) STABLE EMULSIONS OF BACTERIAL ANTIGENS

(71) Applicant: Intervet Inc., Madison, NJ (US)

(72) Inventors: Marco Groot, Beugen (NL); Theodorus Jansen, Venray (NL)

(73) Assignee: Intervet Inc., Rahway, NJ (US)

( * ) Notice: Subject to any disclaimer, the term of this patent is extended or adjusted under 35 U.S.C. 154(b) by 881 days.

(21) Appl. No.: 17/283,053

(22) PCT Filed: Oct. 15, 2019

(86) PCT No.: PCT/EP2019/077898
§ 371 (c)(1),
(2) Date: Apr. 6, 2021

(87) PCT Pub. No.: WO2020/078958
PCT Pub. Date: Apr. 23, 2020

(65) Prior Publication Data
US 2021/0378957 A1 Dec. 9, 2021

(30) Foreign Application Priority Data
Oct. 16, 2018 (EP) .................................... 18200715

(51) Int. Cl.
| | | |
|---|---|---|
| A61K 9/107 | (2006.01) | |
| A61K 39/00 | (2006.01) | |
| A61K 39/12 | (2006.01) | |
| A61K 47/14 | (2017.01) | |
| A61P 31/04 | (2006.01) | |

(52) U.S. Cl.
CPC .............. *A61K 9/107* (2013.01); *A61K 39/00* (2013.01); *A61K 39/12* (2013.01); *A61K 47/14* (2013.01); *A61P 31/04* (2018.01); *A61K 2039/521* (2013.01); *A61K 2039/552* (2013.01)

(58) Field of Classification Search
CPC ........ A61K 9/107; A61K 39/12; A61K 47/14; A61K 2039/521; A61K 2039/552; A61P 31/04
See application file for complete search history.

(56) References Cited

U.S. PATENT DOCUMENTS 5,622,649 A * 4/1997 Hunter .................... A61K 8/064
516/29
6,174,518 B1 * 1/2001 Allard .................... A61K 9/113
424/59

FOREIGN PATENT DOCUMENTS

| EP | 0000424 A1 | 1/1979 |
|---|---|---|
| EP | 1367997 B1 | 8/2009 |
| RU | 2422155 C2 | 6/2011 |
| WO | 9607689 A1 | 3/1996 |
| WO | 02/067899 A1 | 9/2002 |
| WO | 2006113373 A2 | 10/2006 |
| WO | 2008157659 A1 | 12/2008 |
| WO | 2009/032481 A2 | 3/2009 |
| WO | 2014090975 A1 | 6/2014 |
| WO | 2014118385 A1 | 8/2014 |
| WO | 2020078941 A1 | 4/2020 |

OTHER PUBLICATIONS

Aprigny, J.L. and Jaeger, K-E., Bacterial lipolytic enzymes: classification and properties, Biochem. J., 1999, pp. 177-183, 343.
Casiraghi, A. et al., The Influence of the Polar Head and the Hydrophobic Chain on the Skin Penetration Enhancement Effect of Poly(Ethylene Glycol) Derivatives, AAPS PharmSciTech, 2012, pp. 247-253, vol. 13, No. 1.
De Caro, J., et al., Hydrolysis of p-nitrophenyl acetate by the peptide chain fragment (336-449) of porcine pancreatic lipase, Eur. J. Biochem., 1986, pp. 601-607, 158.
De Yan, H. et al., Influence of ammonium salts on the lipase/esterase activity assay using p-nitrophenyl esters as substrates, Biotechnology and applied chemistry, 2013, pp. 343-347, 60.
European Search report for application No. 18200715.3 dated Apr. 8, 2019, 6 pages.
Griffin, W.C., Classification of Surface-Active Agents by "HLB", Journal of Cosmetic Science, 1949, pp. 311-326, 1.
Hasan, F. et al., Methods for detection and characterization of lipases: A comprehensive review, Biotechnology Advances, 2009, pp. 782-798, 27.
Jang, H-J. et al., Safety Evaluation of Polyethylene Glycol (PEG) Compounds for Cosmetic Use, Toxicol. Res., 2015, pp. 105-136, vol. 31, No. 2.
Javed, S., et al., Bacterial lipases: A review on purification and characterization, Progress in Biophysics and Molecular Biology, 2018, pp. 23-34, 132.
Skjold, P. et al., Vaccination against pancreas disease in Atlantic Salmon, *Salmo salar* L., reduces shedding of salmonid alphavirus, Veterinary Research, 2016, pp. 1-6, 47.
Evans, Alfred S., Epidemiological Concepts, Bacterial Infections of Humans—Epidemiology and Control, 2009, 1-50, Chapter 1, 4th Edition.

\* cited by examiner

*Primary Examiner* — Snigdha Maewall
(74) *Attorney, Agent, or Firm* — David J. Kerwick

(57) ABSTRACT

The present invention is based on the discovery of new and advantageous properties of a class of known polymeric emulsifiers. The emulsifier class was found to be resistant to degradation by crude bacterial antigen preparations, which degradation caused emulsion instability when using prior art emulsifiers. This allows the formulation of safe, stable, and effective vaccines based on these emulsions of oil and water comprising such bacterial antigens. The polymeric emulsifier is a block copolymer having a general formula A-B-A in which component B is the divalent residue of a water-soluble polyalkylene glycol and component A is the residue of an oil-soluble complex monocarboxylic acid. Preferred emulsifier is a PEG-30-di-(polyhydroxystearate).

12 Claims, 2 Drawing Sheets

STABLE EMULSIONS OF BACTERIAL ANTIGENS

CROSS-REFERENCE TO RELATED APPLICATIONS

Figure 1:
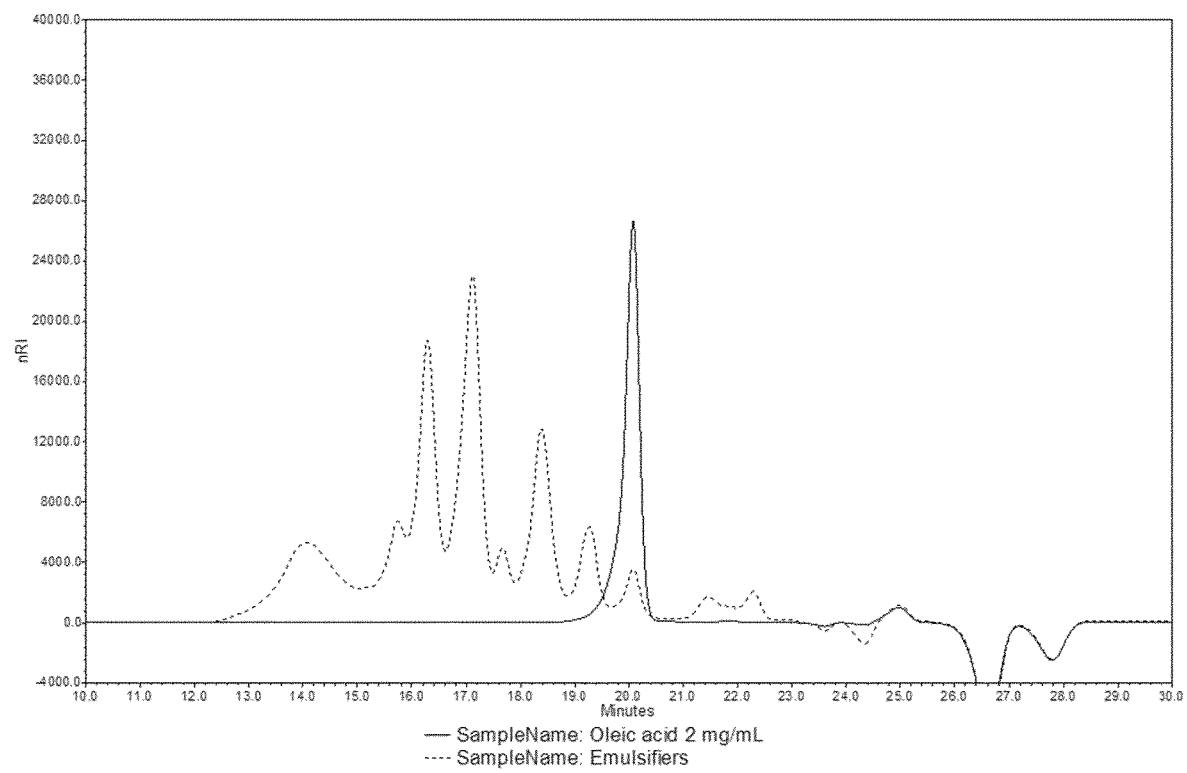
Figure 1B:
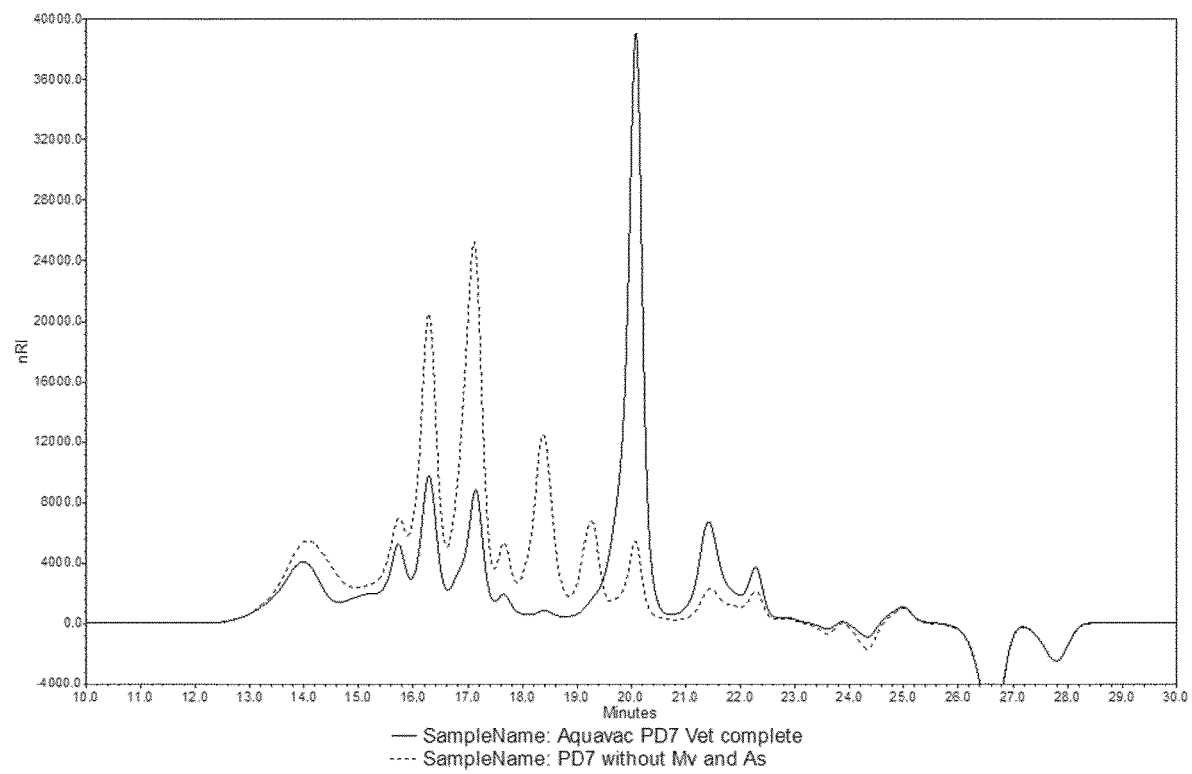
Figure 2:
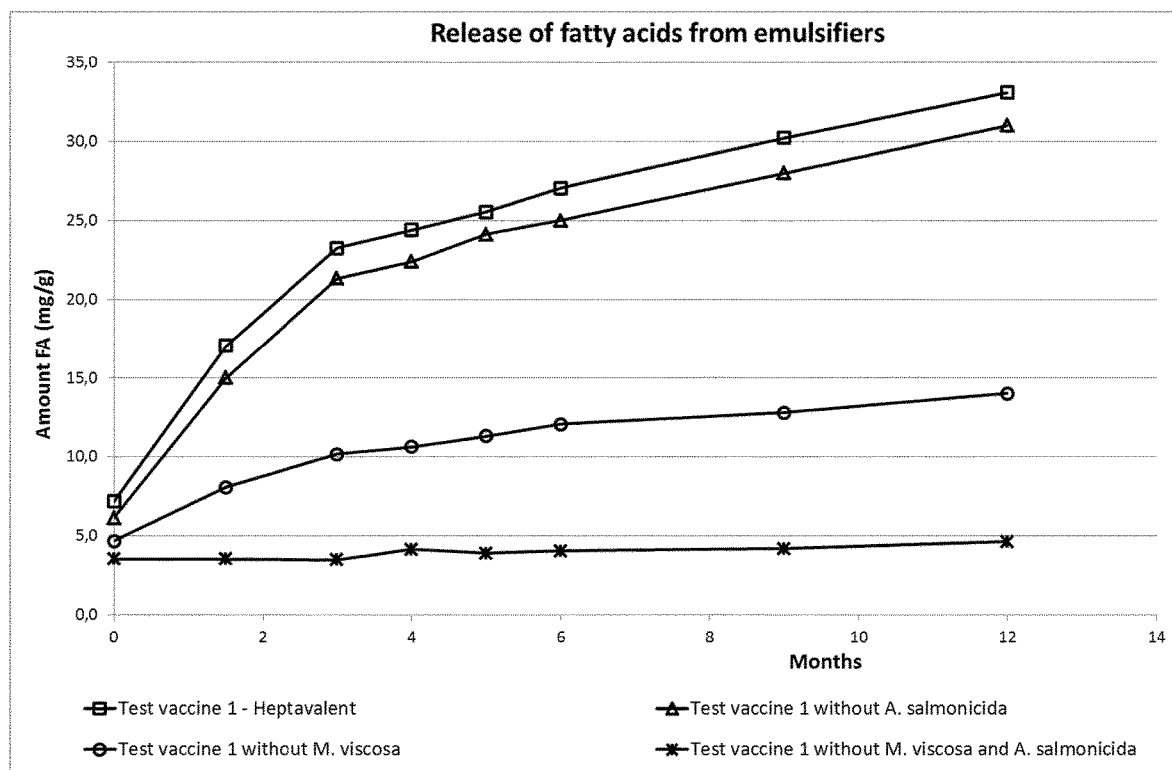

This application is a National Stage entry under 35 U.S.C. § 371 of PCT/EP2019/077898, filed on Oct. 15, 2019, which claims priority to EP application Ser. No. 18/200,715.3, filed on Oct. 16, 2018, the content of PCT/EP2019/077898 is hereby incorporated by reference in its entirety.

The present invention relates to the field of vaccinology, more specifically the invention relates to bacterial vaccines. In particular the invention relates to emulsions with oil- and aqueous phases, an emulsifier, and non-live bacterial antigens; to methods for the manufacture of such emulsions; to vaccines of such emulsions, to a polymeric emulsifier for use in such emulsion vaccines; and to a method of vaccination of such vaccines.

Infections by pathogenic bacteria and their resulting diseases are known since the beginning of civilization, affecting both humans and animals with their often serious effects on health and well-being. Since the mid-20$^{th}$ century, bacterial infections can be effectively treated with antibiotic drugs, although build-up of resistance is a constant threat. The use of antibiotics in animal husbandry in the agricultural sector, is a special situation: on the one hand there is an urgent need for treatment because of a high infection-pressure resulting from the manner and conditions under which animals are often kept. On the other hand the generalised non-therapeutic use of antibiotics, such as in animal feed, is now recognised as one of the causes for increase of resistance in bacteria that are also relevant to human health. As a result such generalised use of antibiotics is being phased-out in more and more countries.

Next to improvements in farm-management, the best alternative for fighting bacterial infection and -disease in a sustainable way, is by vaccination. Bacterial vaccines, both for humans and for animals, are well known for over a century, and are available in many forms. Such vaccines can be live, i.e. contain replicative (attenuated) bacteria, or non-live, i.e. comprise inactivated bacteria, or bacterial components.

Vaccines that comprise non-live antigens often require an immune stimulant for optimal efficacy: an adjuvant. As an excipient, such an adjuvant needs to be pharmaceutically acceptable, and cost effective. Well known adjuvants are aluminium salts and oils. Oil adjuvants can be of mineral or non-mineral origin, whereby mineral oils are generally only allowed for veterinary use.

For ease of administration, and for enhanced adjuvant effect, an oil adjuvant can be emulsified with an antigen in an aqueous phase to form an emulsion that can be used for the preparation of a vaccine. In such emulsion one liquid phase is dispersed in another, typically as a water-in-oil (W/O) or as an oil-in-water (O/W) type emulsion. The choice for one or the other type of emulsion can be based on the type of immune-response that is desired.

To generate and maintain such an emulsion requires the input of both mechanical as well as chemical energy: the separate liquids are mixed in an appropriate device using certain levels of shear-force, pressure, and temperature to disperse one phase into another. The chemical energy is provided by the use of an emulsifier (also: surfactant) which stabilises the dispersed phase by taking position at the interphase of water and oil. A vaccine emulsion can be made up of one or more adjuvants, with one or more emulsifiers.

A large number of emulsifiers for use in emulsion vaccines is available, and more are constantly being developed. A short review of this field was made by Ascarateil & Dupuis (2006, Vaccine vol. 24S2, p. S2/83-S2/85).

Examples of combinations of adjuvants and emulsifiers as used in commercial veterinary vaccines are: Amphigen® (Zoetis), containing a light mineral oil with lecithin as emulsifier; Xsolve® (previously called: Microsol-Diluvac Forte®, MSD Animal health), which contains a combination of the adjuvants light mineral oil and vitamin E-acetate, with the emulsifier Tween® 80 (Polysorbate 80, or polyoxyethylene sorbitan mono-oleate); and MetaStim® (Zoetis), comprising squalane, Pluronic® (a non-ionic tri-block copolymer of blocks of polyoxyethylene and polyoxypropylene), and Tween 80.

An emulsion for use as a vaccine should be stable and not 'break', meaning that the type, size, and number of the droplets of the dispersed phase should not change too much over time, which could eventually lead to reduction of dispersion and increase of phase separation.

Maintaining the stability of the emulsion is important for the use and efficacy of an emulsion vaccine: a sub-optimal distribution of the phases may lead to incorrect dosing, to safety issues, and can affect the immunological potency of the vaccine antigen(s).

Next to the paramount requirements for vaccines to be safe and efficacious, there are some special requirements for vaccines used in animal husbandry. These refer to aspects of ease of use, and especially to costs. This because the production of animal protein is typically a high volume-low margin enterprise. For these reasons, veterinary vaccines will often be directed at several diseases or pathogens at once, by containing several different antigens in a single vaccine formulation. This is favourable to reduce stress for a target animal from prevention of the need for repeated treatments, as well as to reduce labour costs for the administration.

Currently oil-adjuvanted emulsion vaccines with non-live bacterial antigens are commercially available for a large number of pathogens, and for all the major agricultural target species: swine, cattle, sheep, poultry, and fish. Just some examples of such vaccines with complex combinations of antigens are:

PregGuard® GOLD FP 10 (Zoetis) for use in cattle and sheep, containing 4 live attenuated viral antigens, and bacterins from one *Campylobacter* species, and from 5 Leptospira species or subspecies, adjuvated with Amphigen® into an O/W emulsion;

Bovilis® Rotavec® Corona (Coopers) for use in cattle, contains 2 types of each of inactivated Bovine rotavirus and Bovine coronavirus, the toxoids of 2 types of Clostridia bacteria, and *E. coli* pilus antigens absorbed onto aluminium hydroxide; adjuvated with light mineral oil as a W/O emulsion.

Porcilis® Ery+Parvo+Lepto (MSD Animal Health) for swine, comprising inactivated porcine Parvovirus, bacterins of Erysipelothrix, and of 6 serovars of Leptospira, adjuvated with Diluvac Forte® into an O/W emulsion;

Nobilis® Corvac 4 (MSD Animal Health) for poultry, contains bacterins of 4 types of *Haemophilus* (*Avibacterium*) bacteria, adjuvated with light paraffin oil as a W/O emulsion; and AQUAVAC® PD7 Vet (MSD Animal Health) for Atlantic salmon, comprising inactivated antigens of 2 virus species (Infectious pancreatic necrosis virus and Salmon anaemia virus), and of 5 bacterial species or subspecies (*Aeromonas salmonicida* subsp. *salmonicida*, *Vibrio salmonicida*, *Vibrio anguillarum* serotypes O1 and O2a, and *Moritella viscosa*), adjuvated with light paraffin oil in a W/O emulsion.

However not all desired combinations of antigens can be made into stable formulations. This is because of a further consequence of the need to make bacterial vaccines for use in agriculture affordable, namely: that such vaccines will typically not contain expensive pure components (e.g. recombinantly expressed subunits), and cannot be produced using elaborate purification techniques (e.g. column chromatography). In practice this means that the non-live antigens comprised in such vaccines, will typically be relatively impure and of somewhat undefined composition. This applies especially when compared to more purified vaccine antigens in vaccine products of higher market value such as for use in companion animals (cats, dogs, and horses), or even as for use in humans. Alternatively, the specific protective antigen may not be known, so that a crude antigen preparation is the only way to comprise the necessary antigens.

Non-live bacterial vaccines for use in agriculture will therefore typically comprise little purified antigens derived from for example an inactivated bacterial culture or from extracts or fractions of such a culture. Such rather crude antigens can be based on inactivated cells, perhaps washed or concentrated once, or antigen based on bacterial cell-fractions, such as cells that were lysed or disrupted. As a consequence, these crude antigen preparations may contain undefined or unintended impurities which can have an effect on the safety, the efficacy, or the stability of a (combination) vaccine. This is why vaccines as part of their development process, must undergo rigorous testing for safety, efficacy and stability, before they can receive a marketing authorisation from governmental or regulatory authorities to place such vaccine on the market as a commercial product.

The unspecified components of a non-live antigen preparation are not necessarily unwanted, as they may act as a further adjuvant and this way provide an aspecific boost to the immune response. Also, potentially disturbing factors of a biological nature would be expected to become inactivated during the preparation of the non-live bacterial antigens. Nevertheless unwanted effects on safety, efficacy or stability of a vaccine can be observed during the development of an emulsion-based vaccine comprising a crude antigen preparation.

Therefore there is a continued need in this field to provide affordable methods and materials that allow the formulation of safe, stable and effective vaccines that comprise emulsions of non-live bacterial antigens.

It is therefore an object of the present invention to overcome a disadvantage in the prior art, and to accommodate to this need in the field by providing stable emulsions of non-live bacterial antigens that can be used as effective vaccines.

Non-ionic A-B-A block copolymeric emulsifiers of polyalkylene glycol and monocarboxylic acids were first described in EP 0000424 for use in dispersion of water in fuels, and in WO 96/07689 for dispersion of pigments or toners in organic medium. The different uses depend from a difference in molecular weight of the component B.

A practical use for the emulsifiers of EP 0000424 was also found in the cosmetics industry as emulsifiers for skin creams (Jang et al., 2015, Toxicol. Res., vol. 31, p. 105-136). Further, a described pharmaceutical use is for enhancing the skin-penetration of drugs (Casiraghi et al., 2012, AAPS PharmSciTech, vol. 13, p. 247-253).

NB: These emulsifiers are not the same as the non-ionic block copolymeric emulsifiers that are known generally as Poloxamer™ (BASF). The Poloxamers do not contain a fatty acid component A, but are co-polymers of blocks of polyoxyethylene and polyoxypropylene.

WO 2002/067899 describes the use of A-B-A block copolymeric emulsifiers of polyalkylene glycol and monocarboxylic acids in oil emulsion vaccines. The specific disclosure is of the emulsifier Arlacel® P135, and its use in low-viscosity W/O or W/O/W (water-in-oil-in-water) emulsion vaccines with antigens from two inactivated avian viruses.

WO2009/032481 describes a use in agrochemistry of A-B-A block copolymers of polyethylene glycol and 12-hydroxystearic acid. These are used together with a second polymeric emulsifier, to stabilise 0/W emulsions of herbicides against instability arising from crystallisation of ingredients.

During the development of oil-adjuvanted emulsion vaccines with different combinations of non-live viral and -bacterial antigens, the inventors observed occasional failures in the stability of the emulsions. The emulsions were found to break (i.e. showed loss of dispersion, and increase of phase-separation) already after some weeks in stability tests, rendering the vaccine ineffective. Evident possible causes such as poor batch quality of the used mineral oil or of the used pair of emulsifiers (Polysorbate 80 and Sorbitan mono-oleate), were quickly ruled out, leaving the problem unsolved. Without any indication on where to start, began a long search for the reasons for the observed breaking of the emulsion: both for the factor that was affected, and for the factor causing that effect.

Surprisingly it was found that the object can be met, and consequently one or more disadvantages of the prior art can be overcome, by using a polymeric emulsifier of a specific class, namely: a tri-block copolymer of polyalkylene glycol and fatty acids. This was found to solve the occurrence of emulsion-instability, even in complex mixtures, and even when using relatively crude preparations of non-live bacterial antigens.

This finding is hugely beneficial for the development of bacterial vaccines based on emulsions. Especially as it overcomes a need to modify the quality or the composition of the non-live bacterial antigens used in such an emulsion vaccine, thus allowing the use of relatively impure non-live bacterial antigen preparations in emulsion vaccines. In fact, the bacterial antigen can now even be used at a lesser purity than before, and there is no need to establish the level of impurity: all types of bacterial antigens can now be formulated into a stable emulsion according to the invention, using nothing but routine skills.

Thus this is a low cost solution, and further, because this class of polymeric emulsifier is effective at a relatively low weight percentage, this makes available an additional volume in the formulation for the inclusion of antigens.

It is not known exactly how this class of polymeric emulsifiers provides stability to emulsions of oil and water that contain non-live bacterial antigens. Although the inventors do not want to be bound by any theory or model that might explain these findings, they speculate that the sorbitan-based emulsifiers used in the prior art, in particular Polysorbate, were being degraded over time, leading to a loss of emulsifying capacity, and the subsequent breaking of the emulsion. They also speculate that the factors degrading the prior art emulsifies were enzymes that were present in the crude preparation of the non-live bacterial antigens. Of the various enzymes present: proteases, esterases, carbohydrases and nucleases, the esterases may have been the cause for degrading the emulsifiers, considering that an increase in free fatty acids could be observed to correlate with a reduction of the concentration of the prior art emulsifiers in emulsions that showed breaking.

Such bacterial enzymes are produced by many of the known bacterial genera, both Gram positive and Gram negative, and in vivo may serve as virulence factor, and/or to mobilise nutritional components. A review on bacterial esterases is: Arpigny & Jaeger, 1999, Biochem. J., vol. 343, p. 177-183. All major families of bacteria are involved, and both benign or pathogenic strains, such as: *Bacillus, Staphylococcus, Pseudomonas, Salmonella*, and many more. Consequently such enzymes can be present in principle in any preparation of non-live bacterial antigens.

In this respect it is even more surprising that this specific class of polymeric emulsifiers for the invention, was found not to be sensitive to the effect of esterases, considering that these emulsifiers do contain ester bonds!

This was not at all obvious from any disclosure in the prior art, as there is no information on the resistance of this class of polymeric emulsifiers to degradation, in particular to degradation by bacterial enzymes such as esterases. Further, a multivalent emulsion vaccine is a complex formulation with a multitude of biological- and chemical compounds, for which it is very difficult to determine which factor is affected, and which component of the composition is the cause upon the observation of instability of the emulsion.

The large number of potential ingredients in a typical emulsion vaccine with non-live bacterial antigens, of which any one or more can have a negative effect on one of the other components, are for example:
- components of the culture medium used for growing the bacterial culture: e.g. animal serum, broth or extract of animal tissues, peptones or hydrolysates of animal or vegetable origin, lipids, sugars, amino acids, vitamins and minerals, antifoam, antifungals, etc.
- (traces of) inactivating agent: e.g. thiomersal, benzalkonium chloride, formaldehyde, betapropiolactone, or detergent, etc.
- stabilisers: dextrane, glycerol, gelatine, amino acids, buffers, etc.
- preservatives: thiomersal, phenoxyethanol, formaldehyde, antibiotics (e.g. gentamycin),
- components of the bacteria: fragments of the cell wall, the internal cellular organelles, the nucleic acid; external bacterial organelles such as: pili, fimbriae, or flagella; bacterial proteins, lipids, and carbohydrates, such as: toxins, lipopolysaccharides, various enzymes, etc.
- one or more adjuvant(s), emulsifier(s), and their trace elements or impurities.

Further the stability of the emulsion may be affected by one or more effects from physical factors in the preparation, purification, formulation, emulsification, filling, transport and storage of the vaccines.

Therefore in one aspect the invention relates to an emulsion comprising an oil phase, an aqueous phase, an emulsifier and a non-live bacterial antigen, characterised in that the emulsifier is a polymeric emulsifier which is a block copolymer having a general formula A-B-A in which component B is the divalent residue of a water-soluble polyalkylene glycol and component A is the residue of an oil-soluble complex monocarboxylic acid.

An "emulsion" is a mixture of at least two immiscible liquids, whereby one is dispersed in another. Typically the droplets of the dispersed phase are very small, with diameters of a few micrometers or less.

Procedures and equipment for the preparation of an emulsion at any scale are well-known in the art, and are for instance described in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

The term "comprising" (as well as variations such as "comprise", "comprises", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprises" (or its variations) is replaced by terms such as "consist of", "consisting of", or "consist essentially of".

An "oil phase" is a liquid based on an oil. An 'oil' is used here in its common meaning and refers to a nonpolar chemical substance that is hydrophobic and lipophylic, with a high hydro-carbon content. An oil can be of mineral origin, or of non-mineral such as of synthetic, animal or vegetable origin. Some non-mineral oils are metabolisable.

The oil phase may contain excipients such as an emulsifier. Depending on the type of the emulsion, the oil-phase is the continuous phase (as in a W/O emulsion), or is the dispersed phase (as in an O/W emulsion). When used for the formulation of a vaccine, the oil-phase can serve as adjuvant. Much used mineral oil adjuvant in veterinary vaccines is a light (or white) liquid paraffin oil, such as Marcol® (Exxon Mobile) or Drakeol® (Penreco). Common non-mineral oil adjuvants are squalene and squalane (shark liver oil), and tocopherol (Vitamin E).

An "aqueous phase" is a liquid based on water. The aqueous phase may contain e.g. a buffer or saline, and one or more excipients such as an emulsifier or a stabiliser. The aqueous phase may contain the antigen from a fish pathogen for the invention, depending on the type of the emulsion according to the invention.

An "antigen" is a substance that is capable of inducing an immunological reaction in a target human or animal, possibly with the help of an immunostimulating compound such as an adjuvant. Antigens can be prepared synthetically or can be derived from a biological source, for example they can be a micro-organism (replicative or not), or can be a part thereof, e.g. a protein, lipid, carbohydrate, or nucleic acid, or combinations thereof, e.g.: a peptidoglycan, a lipoglycan, a lipopeptide, or a lipopolysaccharide, etc.

A "bacterial antigen" is an antigen that is derived, based, or obtained from a bacterium.

A "non-live bacterial antigen" is any bacterial antigen that is not a live (i.e. not a replicative) bacterium. Often this will be an antigen preparation based on inactivated (killed) bacteria, also called: a bacterin. Such a bacterin will contain inactivated bacterial cells, both whole cells and cells that are more or less damaged or ruptured. A non-live bacterial antigen can also be a part of a bacterial cell, such as: an extract, fraction, homogenate, or sonicate of bacterial cells. Also a non-live bacterial antigen can be a recombinant product, such as an expression vector or an expressed protein. All these are well-known in the art.

For the invention, a bacterium is a prokaryotic microorganism that is currently classified in the taxonomic super kingdom of Bacteria.

The non-live bacterial antigen for the invention is typically contained in a liquid, such as a watery buffer. Depending on the characteristics of the emulsion according to the invention, the non-live bacterial antigen for the invention will either be contained in the internal aqueous phase (in case the emulsion according to the invention is a W/O emulsion), or will be added to the aqueous phase after the emulsification (in case the emulsion according to the invention is an O/W emulsion), as will be outlined below.

An "emulsifier" is a molecule with amphiphilic properties, having both a hydrophobic- and a hydrophilic side. Many emulsifiers are known in the art with their various properties. Most are readily available commercially, and in different degrees of purity.

A compound is "polymeric" when it consists of repeated (molecular) units. As is common with polymeric compounds, the number of subunit repetitions may not be exactly known, but is statistically distributed around an average value lying within a certain range.

The molar ratio between the components A and B may vary from 125:1 to 2:1. The weight proportion of the component B in the polymeric emulsifier for the invention may be up to 80% w/w. The monocarboxylic acid may have up to 25 carbon atoms.

The polymeric emulsifier for the invention is an amphiphilic molecule, in that the components A are "oil-soluble", i.e. have a hydrophobic nature, and the component B is "water-soluble", i.e. is hydrophilic.

The components A and component B each consist of subunits as defined herein which subunits are connected to each other by ether bonds. The components A and B themselves are connected by a —COO— ester bond, making the detailed general structure of the polymeric emulsifier for the invention: A-COO—B—OOC-A.

The term "complex" indicates that the polymer of the monocarboxylic acids, component A, incorporates different monocarboxylic acid moieties, to influence chain-length.

The specific composition of the polymeric emulsifier for the invention can be selected depending on the required emulsifying properties, while considering also: the type of emulsion desired, the type of oil used, and the characteristics of the (multiple) antigen(s) incorporated. For example variations may include the size and composition of components A and B, their molar ratio, and their weight percentage of the complete emulsifier molecule. The properties of those molecules are known, and they are available commercially. All members share the newly discovered and advantageous property of being resistant to degradation by components in non-live bacterial antigen preparations. Consequently, the skilled person is perfectly capable of selecting a particular type of the polymeric emulsifier for the invention to achieve a certain emulsifying effect.

Polymeric emulsifiers for use in the invention are generally available commercially, in different qualities and purities, from a number of suppliers of fine chemicals. Examples are the families of polymers known as: Atlox® and Hypermer® (Uniqema); Termul® (Huntsman); Kolliphor®, Dehymuls®, and Solutol® (BASF); and Cithrol® (Croda).

Also, one or more further emulsifiers can be added, to provide the combination of emulsifiers with certain desired properties. A well-known way to characterise the properties of (mixtures of) emulsifiers is the HLB number (hydrophile-lipophile balance; Griffin 1949, J. Soc. Cosm. Chem., vol. 1, p. 311-326). Typically an emulsifier or emulsifier mixture with HLB number below 10 favours W/O emulsions; an emulsifier (mixture) with HLB number of 10-16 will favour O/W emulsions.

Details of embodiments and of further aspects of the invention will be described below.

The present invention is particularly useful for non-live bacterial antigens that could cause a prior art emulsion of an oil phase and an aqueous phase to break, i.e. antigens that contain an enzyme with esterase activity.

Therefore in an embodiment of the emulsion according to the invention, the non-live bacterial antigen contains an esterase.

An "esterase" for the invention refers to enzymes having esterase activity, specifically to esterases and lipases. Such enzymes are characterised in the IUBMB (International Union of Biochemistry and Molecular Biology) enzyme classification system under EC 3.1.1.1 or EC 3.1.1.3 respectively. Tests to determine whether an antigen "contains an esterase" for the invention, refer to tests for esterase activity which exist in a great variety of forms and types of assays, and are available commercially. Reviews on testing of bacterial esterases are: Hasan et al. (2009, Biotechnol. Adv., vol. 27, p. 782-798), and: Javed et al. (2018, Progr. in Bioph. and Mol. Biol., vol. 132, p. 23-34).

A straightforward detection of esterase activity is by spectrophotometric assay, by detecting a yellow coloration from the release of nitrophenol from a p-nitrophenyl-ester by an active esterase. The paper by De Yan et al. (2013, Biotechn. & Appl. Biochem., vol. 60, p. 343-347) lists several variants of this type of assay in its references no. 2-16. All these are variations on the basic assay as described by De Caro et al. (1986, Eur. J. of Biochem., vol. 158, p. 601-607).

For the invention, to establish whether a non-live bacterial antigen contains an esterase, a detection test is performed according to De Caro et al. (supra), using as substrate: p-nitrophenyl-butyrate. The skilled person is perfectly capable of setting up and performing such a test.

Any level of esterase activity in the bacterial antigen can be harmful to the stability of prior art emulsions, especially upon long term storage. Therefore based on appropriate positive and negative reference standards, the presence of any detectable level of esterase activity qualifies a bacterial antigen as containing esterase according to the invention.

In an embodiment, the emulsion according to the invention does not contain (i.e. is free from) an emulsifier that is susceptible to degradation resulting from a non-live bacterial antigen as defined for the invention; preferably susceptible to degradation by an esterase as defined herein. More preferably, the emulsion is does not contain a sorbate-based emulsifier, or even: does not contain a Polysorbate, more preferably: does not contain a Polysorbate and a Sorbitan mono-oleate.

As described, the advantageous effect of the present invention applies particularly to the use of such emulsions as bacterial vaccines for the agricultural sector. Preferred non-live bacterial antigen for the invention is: an inactivated whole bacterial culture, or is a part of such culture.

Therefore in an embodiment of the emulsion according to the invention, the non-live bacterial antigen is an inactivated bacterial culture, or is a part thereof.

Preferably the part of the inactivated bacterial culture is selected from: a pellet, supernatant, concentrate, dialysate, extract, sonicate, lysate and fraction of such a culture.

What constitutes a "bacterial culture" or "a part thereof" is well-known to a skilled person, and is described in handbooks and manuals such as "Veterinary vaccinology" (supra). For the invention the inactivated bacterial culture is used either as a whole, i.e. as the complete content of a particular culture vessel, or as a part thereof.

Methods and materials to prepare such an inactivated culture or to prepare such a part thereof are generally known and available at any scale. For example: inactivation of bacteria can be performed using chemical or physical means; physical means are e.g. heating, irradiation, or very high pressure; chemical means are e.g. incubation with merthiolate, formalin, diethylamine, binary ethylenamine, beta propiolactone, benzalkonium chloride or glutaraldehyde.

A supernatant or a pellet can be prepared by centrifugation.

A concentrate or a dialysate can be prepared e.g. by a method of cross-flow filtration.

An extract can be made for example by washing or incubation with a solvent or a detergent solution; the solvent can be a liquid or a gas, the liquid can e.g. be aqueous such as water or a buffer; an organic solvent such as an alcohol, acetone, or ether; or can be a supercritical liquid, etc. The extract is the part that is removed with the solvent, and is often retrieved from that solvent in a subsequent process.

A sonicate can be prepared using a sonification device, for example a flow-through sonification cell.

A lysate can be prepared by physical or (bio-)chemical means, e.g. using a French press, or using an enzymatic treatment.

A fraction is a part from a whole that is purified from the rest, for example a filtrate or a precipitate, whereby the fraction is the retentate.

Most used in bacterial vaccines for agricultural use, is a non-live bacterial antigen which comprises inactivated bacterial cells. Commonly such an antigen preparation of killed bacterial cells is called a bacterin.

The inactivated bacterial cells can be in any form, and can be intact or can be damaged. The inactivated bacterial cells can be at any level of purity, for example can be with the bacterial culture medium in which they were fermented, or can be without the culture medium, for example resulting from sedimentation, centrifugation, or concentration.

Therefore in an embodiment of the emulsion according to the invention, the non-live bacterial antigen comprises inactivated bacterial cells.

The bacteria from which the non-live antigen is prepared can be any bacterium of human medical and/or of veterinary relevance, for example any bacterium that is a (potential) pathogen, either as primary- or as secondary (opportunistic) pathogen.

Evidently, combinations of non-live bacterial antigen from two or more bacteria can also be prepared and used. Also, combinations with antigens from viral- or parasitic pathogens are desired.

Preferred emulsions according to the invention are of the W/O type, because these, when used in emulsion vaccines, usually provide a stronger immune stimulation, and of longer duration, as compared to the effect of an O/W emulsion.

Therefore, in an embodiment of the emulsion according to the invention, the emulsion is a water-in-oil (W/O) emulsion.

For the preparation and stabilisation of a W/O emulsion according to the invention, a polymeric emulsifier for the invention is selected with the desired properties, preferably having an HLB number of 10 or less.

Therefore, in an embodiment of the W/O emulsion according to the invention, the components A each have a molecular weight of at least 500 g/mol.

In an embodiment of the W/O emulsion according to the invention, component B has a molecular weight of at least 500 g/mol.

In a preferred embodiment of the W/O emulsion according to the invention, components A and component B all have a molecular weight of at least 500 g/mol.

The W/O emulsion according to the invention may itself be used for the formulation of a further emulsion, such as a W/O/W emulsion. This may require the use of an additional emulsifier, either a version of a polymeric emulsifier for the invention, or another emulsifier. Selection and optimisation of such conditions are within the capabilities of the skilled person.

Preferred components of the polymeric emulsifier for the invention are polyethylene glycol, and polyhydroxystearic acid. Emulsifiers with these building blocks were shown to have favourable properties in regard to the safety of fish vaccines prepared from these emulsions. In addition they provided goof vaccine efficacy, and excellent stability even when the antigens for the invention where (relatively) impure. Also they only require the use of a relatively low weight percentage of the emulsifier, and are effective even at a relatively high amount of water phase dispersed in the oil. This leaves much room for including antigen in aqueous phase into the W/O emulsion according to the invention.

Therefore, in an embodiment of the W/O emulsion according to the invention, component A is a polymer of a hydroxystearic acid.

Preferably the hydroxystearic acid is a 12-hydroxystearic acid.

In an embodiment of the W/O emulsion according to the invention, component B is a polymer of an ethylene glycol.

In a preferred embodiment of the W/O emulsion according to the invention, component A is a polyhydroxystearic acid, and component B is a polyethylene glycol.

Preferably the polyhydroxystearic acid is a poly(12-hydroxystearic acid).

Polyethylene glycol (PEG) is also known as polyethylene oxide (PEO) or polyoxyethylene (POE).

In an embodiment of the W/O emulsion according to the invention, component A is a polyhydroxystearic acid (molecular weight 300 g/mol), and component B is a polyethylene glycol (molecular weight 62 g/mol), whereby component A has 2-50 units of hydroxystearic acid, and component B has 8-60 units of ethylene glycol. For the invention, cited ranges also include the end points.

Especially favourable results in the stabilisation of W/O emulsions according to the invention with relatively impure non-live bacterial antigens, were obtained using as the emulsifier a PEG-30-di-(polyhydroxystearate).

Therefore, in an embodiment of the W/O emulsion according to the invention, the polymeric emulsifier is a PEG-30-di-(polyhydroxystearate).

The term "PEG-30" indicates that the average number of moles of ethylene oxide reacted per mole of substance is: 30.

"PEG-30-di-(polyhydroxystearate)" has CAS nr. 70142-34-6, and has HLB nr. 5.5. Another name for PEG is Macrogol; Macrogol 30 dipolyhydroxystearate is described in the European Pharmacopoiea under monograph no. 07/2011:2584.

PEG-30-di-(polyhydroxystearate) is commercially available, for example as: Cithrol DPHS, Atlox 4912 (Uniqema), Termul 2510, Sabowax PIS, and Dehymuls LE.

Cithrol DPHS (Croda), has an average molecular weight of about 5000 g/mol, and has 5-15 units of 12-hydroxystearic acid per component A, and 15-35 units of ethylene glycol per component B. Previously Cithrol DPHS was known as Arlacel® P135.

NB: Arlacel P135 is not to be confused with Arlacel A, the emulsifier that is used in Freund's complete adjuvants, which is a mixture of a mineral oil and bacteria. Arlacel A is not a block copolymer, but a mono-oleate ester of a mannitol sugar, and has CAS nr. 25339-93-9.

As described in the Examples hereinafter, a stable heptavalent-antigen W/O emulsion could be prepared by using Cithrol DPHS instead of the two prior art emulsifiers: Polysorbate 80 (Tween® 80) and Sorbitan mono-oleate (Span® 80). The resulting O/W emulsion, comprising bacterins of *Moritella* viscose and of *Aeromonas salmonicida* subsp. *salmonicida* was found to be stable for up to three weeks in accelerated stability tests at 37° C., which corresponds to an incubation of 12 to 24 months in real time stability tests at 4° C. The control emulsion with Tween and Span showed complete and irreversible phase separation already after 1 week at 37° C., which corresponds to about 6 months incubation in a real time stability test.

The amount of the polymeric emulsifier for the invention in the emulsion according to the invention is determined based on differences in the desired properties of the resulting emulsion, and of the intended use of the emulsion as a vaccine. The lower limit is determined by the limit of efficacy of the specific polymeric emulsifier used; the upper limit is determined by practical considerations of usability, as some variants of the polymeric emulsifier for use in the invention have a wax-like constitution.

Therefore in an embodiment, the emulsion according to the invention comprises an amount of the polymeric emulsifier for the invention that is 0.01-15% w/w, expressed in weight percent of the vaccine prepared from the emulsion.

Preferably the emulsion according to the invention comprises an amount of the polymeric emulsifier for the invention that is 0.05-10; 0.1-5; 0.2-3; 0.3-2; 0.4-1.5; or even 0.5-1% w/w of the weight of the vaccine prepared from the emulsion, in this order of preference.

In a preferred embodiment, the emulsion according to the invention comprises an amount of the polymeric emulsifier for the invention of about 0.5% w/w, by weight of the vaccine prepared from the emulsion.

For the invention "about" indicates that a number can vary between ±25% around its indicated value. Preferably "about" means±20% around its value, more preferably "about" means±15, 12, 10, 8, 6, 5, 4, 3, 2% around its value, or even "about" means±1% around its value, in that order of preference.

In an embodiment, the emulsion according to the invention comprises an amount of oil of 10-90% w/w; the percentage of oil is expressed by weight of the vaccine prepared from the emulsion.

Preferably the emulsion according to the invention comprises 20-80; 25-70; or even 30-60% w/w, by weight of the vaccine prepared from the emulsion, in this order of preference.

Suitable oil phase for use in the emulsion according to the present invention are mineral- or non-mineral oils, and mixtures of mineral- and non-mineral oils. Mineral oils for the invention include but are not limited to paraffin oils. Non-mineral oils for the invention include but are not limited to vegetable oils, animal oils, natural hydrocarbons, metabolisable synthetic or semi-synthetic oils (such as Miglyol® and Cetiol®), fatty acid esters of propylene glycol and C6 to C24 fatty acids such as oleyl oleates, diesters of capric- or caprylic acids and the like. Suitable vegetable oils for the invention are peanut oil, soybean oil, sunflower oil, and derivatives such as tocopherol. Suitable animal oils for the invention are squalane and squalene and the like. All are widely available commercially.

In an embodiment of the emulsion according to the invention, the oil phase comprises a light mineral oil; preferably the light mineral oil is a liquid paraffin oil.

Such light liquid paraffin oil is generally available, examples are: Drakeol® 6VR (Penreco), Marcol® 52 (Exxon Mobile), and Klearol® (Sonneborn).

When the emulsion according to the invention is intended for use as a vaccine for humans, the use of a mineral oil may not be acceptable.

Therefore in an embodiment of the emulsion according to the invention, the oil phase comprises a non-mineral oil; preferably the non-mineral oil is squalane, squalene, or tocopherol.

In an embodiment the emulsion according to the invention comprises one or more of the features selected from the group consisting of:

- the non-live bacterial antigen contains an esterase;
- the non-live bacterial antigen is an inactivated bacterial culture, or is a part thereof; preferably the part of the inactivated bacterial culture is selected from: a pellet, supernatant, concentrate, dialysate, extract, sonicate, lysate and fraction of such a culture;
- the non-live bacterial antigen comprises inactivated bacterial cells;
- the emulsion is a water-in-oil (W/O) emulsion;
- components A each have a molecular weight of at least 500 g/mol;
- component B has a molecular weight of at least 500 g/mol;
- components A and component B all have a molecular weight of at least 500 g/mol;
- component A is a polymer of a hydroxystearic acid; preferably the hydroxystearic acid is a 12-hydroxystearic acid;
- component B is a polymer of a polyethylene glycol;
- component A is a polyhydroxystearic acid, and component B is a polyethylene glycol; preferably the polyhydroxystearic acid is a poly(12-hydroxystearic acid);
- component A is a polyhydroxystearic acid and component B is a polyethylene glycol, whereby each component A has 2-50 units of hydroxystearic acid, and component B has 8-60 units of ethylene glycol;
- the polymeric emulsifier is a PEG-30-di-(polyhydroxystearate);
- the polymeric emulsifier is Cithrol DPHS;
- the emulsion comprises an amount of the polymeric emulsifier that is 0.01-15% w/w; preferably the emulsion comprises an amount of the polymeric emulsifier that is 0.05-10; 0.1-5; 0.2-3; 0.3-2; 0.4-1.5; or even 0.5-1 w/w by weight of the vaccine prepared from the emulsion, in this order of preference;
- the emulsion comprises an amount of the polymeric emulsifier of about 0.5% w/w by weight of the vaccine prepared from the emulsion;
- the emulsion comprises an amount of oil of 10-90% w/w; preferably the emulsion comprises 20-80; 25-70; or even 30-60% w/w oil, by weight of the vaccine prepared from the emulsion, in this order of preference;
- the oil phase comprises a light mineral oil; preferably the light mineral oil is a liquid paraffin oil; and
- the oil phase comprises a non-mineral oil; preferably the non-mineral oil is squalane, squalene, or tocopherol.

In an embodiment of the emulsion according to the invention the non-live bacterial antigen comprises an esterase and inactivated bacterial cells; the emulsion is a water-in-oil (W/O) emulsion; the polymeric emulsifier is a PEG-30-di-(polyhydroxystearate); the emulsion comprises an amount of the polymeric emulsifier that is 0.5-1 w/w by weight of the vaccine prepared from the emulsion; the emulsion comprises an amount of oil of 30-60% w/w, by weight of the vaccine prepared from the emulsion; and the oil phase comprises a light liquid paraffin oil.

The emulsion according to the invention can be prepared using well-known methods and materials. The details of these procedures will be dependent on the characteristics of the polymeric emulsifier for the invention used, and the type of the emulsion to be prepared. For example, when the emulsion according to the invention is of the O/W type, an emulsion of oil and aqueous phase can be prepared separately, and subsequently the non-live bacterial antigen for the invention is added. However this is usually not applied for an emulsion of the W/O type, where the aqueous phase commonly contains the antigen from the start as it will become the internal phase.

Similarly, when preparing an O/W emulsion, the polymeric emulsifier for the invention is dissolved in the aqueous phase. However when preparing a W/O emulsion, the polymeric emulsifier for the invention is dissolved into the oil phase. Occasionally it may be required to apply some heating of the solvent, for example to 50-60° C., to get the emulsifier completely dissolved. When required, further emulsifiers can be comprised in the oil and/or in the aqueous phase. For both types of emulsions, the aqueous phase and the oil phase can be emulsified using suitable equipment such as by ultrasonic, or rotor-stator type mixing.

For making an O/W type emulsion, where the antigen is initially not present in the aqueous phase, the use of high intensity emulsification of water and oil is a further option, for example using microfluidisation. However, as the skilled person will be well aware, when preparing a W/O emulsion, where the non-live bacterial antigen is comprised in the aqueous phase to be emulsified, the type and the intensity of the emulsification process applied, needs to be compatible with the fragile nature of the antigen to keep its immunological properties intact.

Therefore in a further aspect the invention relates to a method for the manufacture of an oil-in-water (O/W) emulsion according to the invention, the method comprises the steps of:
a. admixing the aqueous phase and the polymeric emulsifier,
b. emulsifying the mixture of step a. with the oil phase, and
c. admixing the emulsion of step b. with the non-live bacterial antigen.

Each of the aqueous phase, the polymeric emulsifier, the oil phase, and the non-live bacterial antigen, are as defined hereinabove.

In a similar aspect, the invention relates to a method for the manufacture of the W/O emulsion according to the invention, the method comprising the steps of:
a. admixing the oil phase and the polymeric emulsifier, and
b. emulsifying the mixture of step a. with the aqueous phase, whereby the aqueous phase comprises the non-live bacterial antigen.

Again, each of the oil phase, the polymeric emulsifier, the aqueous phase, and the non-live bacterial antigen, are as defined hereinabove.

Preferably the method for the manufacture according to the invention is performed in a way that allows a medical use of the emulsion produced, such as in a vaccine. Commonly this regards the use of equipment and ingredients that are pharmaceutically acceptable, and complying with quality regulations such as good manufacturing practice standards. All these are well known to a skilled person, and are prescribed in Governmental regulations such as the Pharmacopoeia, and in handbooks such as: Remington and Pastoret (both supra). Typically such manufacture is done aseptically.

As described, the emulsion according to the invention is particularly advantageous when applied as a vaccine against bacterial disease.

Therefore, in a further aspect the invention relates to the emulsion according to the invention for use as a vaccine for the protection of a human or animal target against infection or disease caused by a bacterium.

In a further aspect the invention relates to the emulsion according to the invention for use in the vaccination of a human or animal target against infection or disease caused by a bacterium.

In a further aspect the invention relates to a vaccine for use in the protection of a human or animal target against infection or disease caused by a bacterium, characterised in that the vaccine comprises the emulsion according to the invention.

As the skilled person will be well aware, the emulsion according to the invention can be applied "for use as a vaccine" in different ways. For example, the emulsion itself can be applied as a vaccine. Alternatively the emulsion can be used as ingredient in further processing for example into a W/O/W emulsion, which can then be applied as a vaccine. Also, the use as a vaccine may require admixing or including certain further ingredients, for example stabilisers or preservatives. Preservatives are e.g. thiomersal, phenoxyethanol, formalin, antibiotics (e.g. gentamycin). Stabilisers are e.g. dextrane, glycerol, gelatine, amino acids, or buffers. Depending on the type of the emulsion, the further ingredients may be added during- or after the manufacture of the emulsion according to the invention.

A "vaccine" is a well-known composition with a medical effect, and comprises an immunologically active component, and a pharmaceutically acceptable carrier. As 'carrier' for the invention functions the aqueous phase, or the emulsion itself. The 'immunologically active component' for the invention is the non-live bacterial antigen. The vaccine stimulates the immune system of a target human or animal, and induces a protective immunological response. The response may originate from the targets' innate- and/or from the acquired immune system, and may be of the cellular- and/or of the humoral type.

A vaccine provides "protection" "against infection or disease" by reducing in a vaccinated target the severity of a subsequent infection, by for example reducing the number of pathogens, or shortening the duration of the pathogen's replication in the target, and reducing the number, the intensity, or the severity of lesions caused by a bacterial infection. Also, or consequentially, a vaccine is effective in reducing or ameliorating the (clinical) symptoms of disease that may be caused by such infection or replication, or by the target's response to that infection or replication. A reference for such diseases and clinical signs is: "The Merck veterinary manual" (10th ed., 2010, C. M. Kahn edt., ISBN: 091191093X. Such a vaccine is colloquially referred to as a: vaccine 'against' the particular bacterium, or as a 'bacterial vaccine'.

In order to be immunologically effective, a vaccine needs to contain a sufficient amount of the antigen. How much that is, is either already known from related vaccines, or can readily be determined e.g. by monitoring the immunological response following vaccination and (in the case of an animal target) a challenge infection, e.g. by monitoring the targets' signs of disease, clinical scores, or by re-isolation of the pathogen, and comparing these results to a vaccination-challenge response seen in mock-vaccinated animals.

The amount of the non-live bacterial antigen for the invention can be expressed in different ways, depending on the type of the antigen employed. For example the antigen dose can be expressed as a number of bacterial cells, counted before they were inactivated. Alternatively the antigen can be quantified by a serologic- or bio-chemical test such as an ELISA or an AlphaLisa™, and expressed in relative units, compared to an appropriate reference standard. All these are well known in the art.

The vaccine according to the invention can be used as a prophylactic-, metaphylactic-, or therapeutic treatment.

The vaccine according to the invention can serve as an effective priming vaccination, which can later be followed and amplified by a booster vaccination, with the same or with a different vaccine.

The vaccine according to the invention can additionally comprise other compounds, such as an additional antigen or micro-organism, a cytokine, or an immunostimulatory nucleic acid comprising an unmethylated CpG, etc. Alternatively, the vaccine according to the invention, may itself be added to a vaccine.

The vaccine according to the invention can advantageously be combined with one or more further antigens, e.g. derived from a micro-organism pathogenic to the intended human or animal target. Such a further antigen may itself be an infectious micro-organism, or be inactivated, or a subunit. The further antigen may consist of a biologic or synthetic molecule such as a protein, a carbohydrate, a lipopolysaccharide, a lipid, or a nucleic acid molecule.

Therefore, in an embodiment, the vaccine according to the invention comprises at least one additional antigen.

The targets for the vaccine according to the invention are humans or animals in need of a vaccination against infection or disease caused by the particular bacterium from which a non-live antigen is comprised in the vaccine. The age, weight, sex, immunological status, and other parameters of the target to be vaccinated are not critical, although it is clearly favourable to vaccinate healthy, uninfected targets, and to vaccinate as early as possible.

An "animal" for the invention is any animal of veterinary relevance, e.g. bovine, porcine, caprine, ovine, cervine, canine, feline, equine, avian, fish, or shrimp.

The selection of the target for vaccination is determined by the host range of a bacterium: for humans, for animals, or for both. Alternatively a bacterium can be pathogenic to humans but not to an animal carrying the bacterium. In that case it may still make sense to apply animal vaccination, in order to prevent zoonotic infection and food-borne illness of humans that would otherwise consume an infected animal product such as e.g. meat, milk, or eggs.

Therefore in a preferred embodiment of the vaccine according to the invention, intended for a human and/or an animal target, the non-live bacterial antigen for the invention is derived from a bacterium from a bacterial family of: *Staphylococcus, Streptococcus, Bacillus, Neisseria, Salmonella, Shigella, Listeria, Escherichia, Campylobacter, Clostridium, Mycobacterium, Pseudomonas, Leptospira, Legionella, Helicobacter, Bartonella, Bordetella, Borrelia, Brucella, Burkholderia, Chlamydia, Coxiella, Corynebacterium, Enterococcus, Francisella, Haemophilus, Mycoplasma, Treponema, Vibrio, Yersinia, Actinomyces, Bacteroides, Corynebacterium, Ehrlichia, Klebsiella, Nocardia, Rickettsia, Lactobacillus, Anaplasma* (*Ehrlichia*), and *Actinobacterium*.

The names indicated above refer to the bacterial families to which these bacteria are currently assigned. However that is a taxonomic classification that could change in time as new insights can lead to reclassification into a new or different taxonomic group. However, as this does not change the bacterium itself, or its antigenic repertoire, but only its scientific name or classification, such re-classified bacteria remain within the scope of the invention.

The reference to a bacterial family includes any bacterium that is a species, subtype, variant, biotype, serotype or genotype within that family.

Such bacteria for the preparation of a non-live bacterial antigen for the invention can be obtained from a variety of sources, e.g. as field isolate from a human or from an animal in the wild or on a farm, or from various laboratories, (depository) institutions, or (veterinary) universities.

As described, the vaccine according to the invention is of particular relevance in the field of animal husbandry.

Therefore in an embodiment, the vaccine according to the invention is for the protection of an animal target against infection or disease caused by a bacterium.

Consequently, for the different groups of animal targets, the non-live bacterial antigen for the invention is derived from a bacterium from a bacterial family as indicated:

For vaccination of ruminants the bacterium is selected from one of: *Pasteurella, Escherichia, Salmonella, Yersinia, Staphylococcus, Streptococcus, Mycobacterium, Moraxella, Bacillus, Brucella, Clostridia, Mannheimia, Haemophilus, Francisella, Fusobacterium, Histophilus, Fusobacterium, Trueperella* (Arcanobacterium), *Actinomyces, Clostridium, Coxiella, Campylobacter, Erysipelothrix, Leptospira, Listeria, Burkholderia, Nocardia, Mycoplasma, Bacteroides*, and *Chlamydia*.

For vaccination of porcines the bacterium is selected from one of: *Mycoplasma, Lawsonia, Escherichia, Brachyspira, Streptococcus, Salmonella, Clostridium, Actinobacillus, Pasteurella, Haemophilus, Erysipelothrix, Leptospira, Burkholderia, Enterococcus, Mycobacterium*, and *Bordetella*.

For vaccination of poultry the bacterium is selected from one of: *Escherichia, Salmonella, Staphylococcus, Streptococcus, Ornitobacterium, Avibacterium, Haemophilus, Pasteurella, Erysipelothrix, Mycoplasma, Mycobacterium, Clostridium, Campylobacter, Shigella, Borrelia, Enterococcus, Listeria, Riemerella, Bordetella*, and *Clostridium*.

For vaccination of an animal of aquatic nature, the bacterium is selected from one of: *Aeromonas, Vibrio, Moritella, Edwardsiella, Francisella, Flexibacter, Pasteurella, Cytophaga, Corynebacterium, Renibacterium, Arthrobacter, Flavobacterium, Fusarium, Bacillus, Yersinia, Mycobacterium, Neorickettsia, Listonella, Flexibacter, Piscirickettsia, Streptococcus, Shewanella, Pseudomonas, Photobacterium, Clostridium, Tenacibaculum, Lactococcus, Leucothrix*, and *Nocardia*.

Considering that the economic margins on vaccines for use in aquaculture are the lowest in the field of animal husbandry, the advantageous effects of the present invention are especially beneficial for utilisation in this area.

Therefore, in a preferred embodiment of the vaccine according to the invention for the protection of an animal target, the animal target is a fish.

A "fish" refers to fin fish, both cartilaginous and bony fin fish, of any climate area: cold-, temperate- or tropical waters, and living in sweet-, brackish, or salt water. The fish may be grown in captivity as farmed fish, breeding fish or ornamental fish. Preferably a fish is selected from: bass, grouper, snapper, Tilapia, yellowtail, amberjack, flounder, Pangasius, carp, bream, sturgeon, catfish, eel, trout, salmon, whitefish, halibut, cod, Koi, and goldfish.

In an embodiment the fish is a salmonid fish; preferably the salmonid fish is selected from Atlantic-, steelhead-, chinook-, coho-, pink-, chum-, and sockeye salmon, rainbow-, brook-, lake-, and brown trout, and char.

As described, the emulsion according to the invention allows for the use of a relatively large volume of water as compared to the oil. This is favourable for including a relatively large mass of aqueous phase containing antigen in the vaccine that is prepared from the emulsion according to the invention.

Therefore in a preferred embodiment of the vaccine according to the invention, the ratio of water:oil in the vaccine is 40:60% w/w or is higher with respect to the relative amount of the water. The % w/w is expressed by weight of the vaccine.

More preferably the water:oil ratio in the vaccine according to the invention is 45:55, 50:50, 55:45, 60:40, 65:35, 70:30, 75:25, 80:20, 85:15, or even 90:10% w/w expressed by weight of the vaccine, in this order of preference.

For ease of handling, and to facilitate the use of the vaccine according to the invention, and specifically of its administration by injection, the emulsion vaccine should not have a viscosity that is too high. In addition, by choosing a certain viscosity, the occurrence of sedimentation or creaming of the dispersed phase in the emulsion vaccine can be reduced or prevented.

Therefore in an embodiment the vaccine according to the invention has a viscosity below 500 mPa·s.

Preferably the vaccine has a viscosity of less than 400 mPa·s., less than 300 mPa·s., or even between 100 and 300 mPa·s., in this order of preference.

Such viscosity is to be determined at about 20° C., using a Brookfield DV-I+ viscometer, utilising spindle type No. 62 for 30 sec. at 60 r.p.m.

Methods and materials to influence the viscosity of an emulsion (vaccine) of an oil phase and an aqueous phase, are well-known to a skilled person. For example by varying the amount of water in the emulsion, or the size of the droplets of the dispersed phase.

Therefore in an embodiment of the vaccine according to the invention, the mean droplet size (diameter) of the dispersed phase is less than 25 μm.

Methods and equipment to measure particle sizes are well-known, and can for example employ laser-light scattering measurements.

In a preferred embodiment of the vaccine according to the invention, the mean droplet size (diameter) of the dispersed phase is less than 20 μm; less than 15 μm, less than 10 μm, between 10 and 0.1 μm; or even between 5 and 0.5 μm, in this order of preference;

In a preferred embodiment the vaccine according to the invention is based on a W/O emulsion; comprises a mineral oil as the oil-phase; comprises 0.5-1% w/w expressed by weight of the vaccine PEG-30-di-(polyhydroxystearate) as emulsifier; has a water:oil ratio of 60:40-70:30% w/w expressed by weight of the vaccine; has a viscosity below 400 mPas; and has a mean droplet size (diameter) of the dispersed phase of 20 μm or less.

It is well within reach of the skilled person to further optimise a vaccine according to the invention. Generally this involves the fine-tuning of the efficacy of the vaccine to further improve its provided immune-protection. This can be done by adapting the dose, volume, adjuvant or antigen content of the vaccine, or by application via a different route, method, or regime. All these are within the scope of the invention.

Further aspects of the present invention relate to novel and inventive uses and combinations of the elements of the invention such as the polymeric emulsifier and the non-live bacterial antigen, both for the invention.

Therefore, in a further aspect the invention relates to a polymeric emulsifier for use in an emulsion vaccine, the emulsion vaccine comprising an oil phase and an aqueous phase, the polymeric emulsifier is as defined herein, characterised in that the emulsion comprises a non-live bacterial antigen.

In a further aspect the invention relates to a use of the polymeric emulsifier as defined herein, for the manufacture of an emulsion of an oil phase, an aqueous phase, and a non-live bacterial antigen.

In a further aspect the invention relates to a use of a non-live bacterial antigen for the manufacture of an emulsion of an oil phase and an aqueous phase, which emulsion comprises the polymeric emulsifier as defined herein.

The vaccine according to the invention needs to be administered to a human or animal target, in order to achieve its beneficial immunogenic effect.

Therefore, in a further aspect the invention relates to a method for the vaccination of a human or animal target against infection or disease caused by a bacterium, the method comprising the administration to said target of the vaccine according to the invention.

The "administration" of the vaccine according to the invention to a human or animal target can be performed using any feasible method and route. Typically the optimal way of administration will be determined by the type of the vaccine applied, and the characteristics of the target and the bacterial disease that it is intended to protect against. Depending on whether the vaccine according to the invention is based on an O/W or on a W/O emulsion, different techniques of administration can be applied. For example as an O/W emulsion vaccine the vaccine according to the invention can be administered by enteral or mucosal route, i.e. via eye drop, nose drop, oral, enteric, oro-nasal drop, spray. Other possibility is via a method of mass administration, such as via drinking water, coarse spray, atomisation, on-feed, etcetera.

Preferred way of administration for a method of vaccination according to the invention is by parenteral route.

"Parenteral" refers to administration through the skin, for example by intramuscular, intraperitoneal, intradermal, submucosal, or subcutaneous route.

It goes without saying that the optimal route of administration of a vaccine according to the invention will depend on the specifics of the vaccine that is used, and on the particular characteristics of the target. A skilled person is perfectly capable of selecting and optimising such route and method of administration.

The volume of a dose of the vaccine according to the invention, e.g. when administered by parenteral route, is a volume that is acceptable for the target human or animal, and can for instance be between about 0.1 and about 10 ml. Preferably one dose is a volume between 0.1 and 5 ml, more preferably one dose is between 0.2 and 3 ml.

When administered by intramuscular route, the volume of one dose is preferably between about 0.5 and about 3 ml, more preferably between 1 and 2 ml.

When administered by intradermal route, the volume of one dose is preferably between about 0.1 and about 0.5 ml, more preferably about 0.2 ml.

The method, timing, and volume of the administration of a liquid vaccine composition according to the invention is preferably integrated into existing vaccination schedules of other vaccines that the target human or animal may require, in order to reduce stress to the target and to reduce labour costs. These other vaccines can be administered in a simultaneous, concurrent or sequential fashion, in a manner compatible with their registered use.

The invention will now be further described by the following, non-limiting, examples.

EXAMPLES

1. Example 1: Analysis of Prior Art Emulsions

To analyse why the prior art emulsion vaccines were breaking, the stability was analysed of such emulsion vaccines comprising crude non-live bacterial antigens, with Polysorbate 80 and Sorbitan mono-oleate as emulsifiers. The test vaccines used comprised a 7 way combination of antigens, from viral and bacterial origins, comparable to prior art vaccines, and contained identical quantities of the following inactivated antigens per dose (0.1 ml) of vaccine:

Salmon pancreas disease virus (SPDV), strain F93-125, ≥75% RPP (1)
Infectious pancreatic necrosis virus (IPNV), serotype Sp, ≥1.5 ELISA units (2)
*Aeromonas salmonicida* subsp. *salmonicida,* ≥10.7 log 2 ELISA units (3)
*Vibrio salmonicida,* ≥90% RPS (4)
*Vibrio* anguillarum serotype O1, ≥75% RPS
*Vibrio* anguillarum serotype O2a, ≥75% RPS
*Moritella viscosa,* ≥5.8 log 2 ELISA units (3)

(1) RPP: relative percentage protection in a laboratory test in Atlantic salmon
(2) antigen amount measured in finished product
(3) serological response in Atlantic salmon
(4) RPS: relative percent survival in a laboratory test in Atlantic salmon The test vaccines were formulated as water-in-oil emulsions, with light liquid paraffin oil as adjuvant, and contained as emulsifier either Polysorbate 80 and sorbitan mono-oleate, or contained 0.5% w/w Cithrol DPHS as emulsifier. Water:oil weight ratio of the vaccine was 45:55.

Variations were tested in regard to the presence of the *M. viscosa* antigen and/or the *A. salmonicida* antigen:

1. test vaccine with heptavalent antigens, as a W/O emulsion, using Tween 80 and Span 80 emulsifiers
2. test vaccine 1, but without *M. viscosa* antigen
3. test vaccine 1, but without *A. salmonicida* antigen
4. test vaccine 1, but without *M. viscosa* and without *A. salmonicida* antigens In corresponding accelerated stability tests, the vaccine no. 1 showed breaking of the emulsion already after 1 week at 37° C., vaccines 2 and 3 showed breaking after 2-3 weeks, and vaccine 4 remained stable for the full 3 weeks at 37° C.

The vaccines were then analysed for any increase in the level of free fatty acids during real time stability tests at 4° C. over several months. This increase could give an indication of the degradation of the emulsifiers (Polysorbate 80 and sorbitan mono-oleate) over time. At the different time points samples were drawn and analysed using solid phase extraction (SPE) followed by size exclusion chromatography (SEC). In short: the various samples were loaded on a silica SPE cartridge, and the fatty acids were eluted using methanol. Subsequently, size exclusion separation was done on this eluate using an HPLC system (Agilent™ 1200) with Oligopore™ gel permeation columns at 35° C. and at 50 bar. An Isocratic mobile phase of tetrahydrofuran/acetic acid was used, and detection was by refractive index. For calibration, samples of oleic acid at 1 or 2 mg/ml were used. Positive control was a sample containing Polysorbate 80 and sorbitan mono-oleate at the same concentrations as in the test vaccine emulsions.

Overlay chromatograms comparing the fatty acid peak patterns of the samples tested in stability assay are provided in FIG. 1 panels A and B. From the chromatograms, the results of the calibration samples of oleic acid were used to calculate the amount of free fatty acids in mg/g in the other test samples. These calculated amounts of free fatty acids formed in the different test vaccines over time at 4° C., are represented in FIG. 2.

1.1. Results:

The overlay chromatogram in FIG. 1—panel A shows the fatty acid peak patterns as obtained from the testing of oleic acid (solid line) and of the control sample of the prior art emulsifiers in unaffected form (dotted line). While the oleic acid eluted as a single peak at about 20 minutes elution time, the prior art emulsifiers eluted between 15 and 22 minutes in a specific pattern with multiple peaks.

FIG. 1—panel B compares the fatty acid peak patterns measured of samples from test vaccines 1 (heptavalent W/O emulsion vaccine-solid line) and 4 (test vaccine without antigens of *M. viscosa* and of *A. salmonicida*—dotted line), after 12 months at 4° C.:

For test vaccine 4, the specific peak pattern corresponding to the prior art emulsifiers can clearly be seen between 15 and 22 minutes, and no increase of the oleic acid peak at 20 minutes was detected. Consequently in this emulsion vaccine the emulsifiers were not degraded, and this corresponded with the observed continued stability of this vaccine.

The sample of test vaccine 1 did still show some pattern of the emulsifiers, but at reduced height, and in addition showed a strongly increased peak at 20 minutes. This demonstrated the generation of oleic acid, resulting from the degradation of the emulsifiers, which correlated with the observed instability of the full heptavalent vaccine-emulsion over time.

A similar result is presented by FIG. 2, which clearly shows that the cumulative formation of free fatty acids, and thus the degradation of the emulsifiers, in the vaccine 4 (without *A. salmonicida* and without *M. viscosa* antigens) is negligible. However in vaccines 1-3, comprising *M. viscosa* and/or *A. salmonicida* antigens, significant amounts of free fatty acids are released in the first few months of storage. This continues at a slower rate in subsequent months. Also, the degradation caused by the *A. salmonicida* antigen is less severe than that caused by the *M. viscosa* antigen.

1.2. Conclusions

In the emulsion vaccines tested, a release of free fatty acids over time could be observed, at the expense of a degradation of the emulsifiers. This correlated with the observed breaking of the emulsion in stability testing. Responsible for the degradation of the emulsifiers was the presence of non-live bacterial antigens from the bacteria M. viscose or *A. salmonicida.*

Consequently, it was demonstrated that instability of emulsion vaccines comprising an oil phase and an aqueous phase can be caused by the presence of non-live bacterial antigens, which caused a degradation of the emulsifiers Polysorbate 80.

2. Example 2: Efficacy Trials

2.1. Introduction

The following experiment was performed to test if there were consequences for the vaccine's efficacy from the replacement of the prior art emulsifiers Tween 80 and Span 80, by Cithrol DPHS as emulsifier. The experimental vaccines tested comprised several antigens, mineral oil as adjuvant, and were formulated as water-in-oil emulsions.

Aspects of the safety of these emulsion vaccines were also studied, but these are only reported here very briefly.

2.2. Materials and Methods

2.2.1. Experimental Design

For assessing the serological response after vaccination, Atlantic salmon parr (of approximately 35 grams) were treated one week before vaccination with an increase of their water temperature from 12° C. to 17° C., by adjusting +2° C. every second day. Next the fish were intraperitoneally vaccinated with vaccines Hepta-P (heptavalent antigen containing emulsion, with polysorbate and sorbitan-oleate as emulsifiers), or Hepta-C (similar vaccine, comprising Cithrol as emulsifier), as test groups. A control group was also included that was injected with saline. The three groups, each consisting of 50 fish, were kept in separate tanks at 17° C. during the nine weeks immunization period. The fish were observed daily.

At 9 weeks pv, blood was sampled from 35 fish from each group. Immune response against *Aeromonas salmonicida* and *Moritella viscosa* were evaluated by performing ELISA's on individual serum samples.

2.2.2. Test Vaccines

Both test vaccines Hepta-P and Hepta-C contained the same 7 antigens as also comprised in the test vaccine 1 described in Example 1 above. Mock vaccine was sterile saline (0.9% NaCl).

The vaccine bottles were incubated overnight at ambient temperature (15° C.) and hand-shaken prior to use.

2.2.3. Test Animals

Atlantic salmon, strain: Stofnfiskur, Iceland, of mixed sex, and mean weight at vaccination was 33.5 grams (n=20).

Test animals were given 7 days of acclimatisation at experimental conditions.

Routine disease monitoring was performed on the experimental population by a veterinarian responsible for fish health. In addition, the batch of experimental fish used, tested negative for IPNV, SPDV and ISAV by PCR.

The vaccinated salmon were individually marked by maxillae clipping or adipose fin clipping; the salmon injected with the control substance remained unlabelled.

Test animals were kept in fresh water tanks, at 17° C.±2° C. with at least 85% oxygen, or at 12° C.±2° C. with at least 75% oxygen, pH=6.8-7.2.

Feed was commercial fish feed, available to appetite. Feeding and environmental controls were carried out daily. After vaccination, the fish were observed until they had properly recovered from anaesthesia.

2.2.4. Vaccination

Prior to vaccination the experimental fish were starved for 36 hrs and anaesthetized. The test- and the control groups were given the vaccine or control substance by i.p. injection, at 0.1 ml/dose, using single use syringes of 0.5×4 mm.

2.2.5. Monitoring of Results

Further serology data were collected from the fish kept at 17° C.: blood was collected at 9 w. pv. from 35 fish from each test group kept at 17° C., and of 12 fish from the control group. After overnight clotting, the sera were mixed 1:1 with 86% glycerol and stored at −20° C. until analysis by ELISA.

The Elisa methods applied are the standard tests for these antigens, and are well-known to be indicative of in vivo efficacy.

Antibodies against *M. viscosa* in serum were measured using a direct ELISA. In short, ELISA plates were coated with inactivated *M. viscosa* and test and control sera were added in serial two-fold dilutions to the plate. Bound antibodies were detected using rabbit anti-salmon IgM, followed by HRP-conjugated mouse anti-rabbit IgG. A colour reaction reflecting bound salmon antibodies was developed by adding a TMB substrate, and the colour measured using an ELISA reader. The antibody titre was expressed as Log 2 value of the maximum dilution of the sample that gave an OD-value equal to 3 times the mean found for a negative control serum measured on each plate.

Antibodies against *A. salmonicida* in serum were measured using a similar direct ELISA as described for *M. viscosa*, except that the ELISA plates were coated with inactivated *A. salmonicida*. The antibody titre was expressed as Log 2 value of the maximum dilution of the sample that gave an OD-value equal to 5 times the mean found for a negative control serum measured on each plate.

The antibody titres were calculated using the CBA™ program (Abend Vertical) and the titres were expressed in Log 2 values as the maximum dilution giving 5 times the mean background. Validity was based on the scores of test- and control samples being within certain value ranges.

2.3. Results and Discussion

2.3.1. Results of Tests for Safety and Serology at 9 w pv and 17° C.

2.3.1.1. Antibody Response Against *A. salmonicida* at 9 w pv

Specific antibodies against *M. viscosa* and *A. salmonicida* were measured in the same sera.

The antibody titres against *A. salmonicida* induced by the Hepta-C vaccine were significantly higher than those induced by the Hepta-P vaccine (ANOVA, p<0.0001), while the antigens used and their amounts were the same. Both vaccines induced titres that were above the potency requirement (10.7 Log 2).

As is also evident from the smaller standard deviation, the antibody titres induced by the Hepta-C vaccine also showed less spread between fish than for the Hepta-P vaccinates.

The ELISA titres in the saline group were below the detection limit (6.6). Results are presented in Table 1.

Both vaccine groups induced significantly increased antibody titres as compared to the control group. Whereby the Hepta-C vaccine performed even better than the Hepta-P vaccine in regard to efficacy against *A. salmonicida*.

TABLE 1

Serology results against A. salmonicida at 9 w pv, and at 17° C.

| Group | Log2 Ab titre against A. salmonicida | |
|---|---|---|
| | mean | stand. dev. |
| Hepta-P (Tween + Span) | 13.0 | 1.8 |
| Hepta-C (Cithrol) | 15.2 | 1.2 |
| Saline | ≤6.6 | 0.0 |

2.3.1.2. Antibody Response Against *M. viscosa* at 9 w pv

For the induction of seroresponse against *M. viscosa*, a similar picture emerged as for *A. salmonicida*: the titres induced by the Hepta-C vaccine were significantly higher (ANOVA, p<0.0001) and with less spread, than the titres induced by the Hepta-P vaccine, even though both contained the same antigens and at the same amounts. Results are presented in Table 2. Both vaccines induced titres that were above the potency requirement (5.8 Log 2).

Both vaccine groups induced significantly increased antibody titres as compared to the control group.

Again, both vaccine groups induced significantly increased antibody titres as compared to the control group. Whereby the Hepta-C vaccine performed even better than the Hepta-P vaccine in regard to efficacy against *M. viscosa*.

TABLE 2

Serology results against M. viscosa at 9 w pv, and at 17° C.

| Group | Log2 Ab titre against M. viscosa | |
|---|---|---|
| | mean | stand. dev. |
| Hepta-P (Tween + Span) | 8.3 | 1.8 |
| Hepta-C (Cithrol) | 11.9 | 1.2 |
| Saline | ≤4.6 | 0.0 |

2.3.1.3. Aspects of Safety

Certain vaccination side-effects, typical for the use of oil-emulsion vaccines in salmon, were scored at 9 weeks post vaccination: intra-abdominal adhesions and melanisation. Both were well within acceptable levels, and no significant differences were found between the two groups receiving the test vaccines, for either of these side-effects.

2.4. Conclusions

The efficacy profile of the Cithrol-based heptavalent vaccine formulation is at least as good as that of the similar vaccine emulsified with Tween 80 and Span 80, because the Hepta-C vaccinates showed significantly better immune-response against *A. salmonicida* and against *M. viscosa*; both with higher antibody titres and with smaller spread. Aspects of vaccine-safety were also not changed.

3. Example 3: Efficacy Against SPDV

3.1. Introduction

In this experiment the inventors expanded on the efficacy results as described in Example 2 above. Using the exact same vaccine formulations the protective capacity was tested against a challenge infection with salmon pancreas disease virus (SPDV). The side-by-side comparison was made between a prior art formulation of a heptavalent vaccine with Tween 80+Span 80 emulsifiers, against a heptavalent vaccine based on the novel emulsion with Cithrol DPHS as emulsifier. Vaccinations used only a half dose per animal, conform the registered potency test for release of efficacious batches of SPDV vaccines.

3.2. Materials and Methods

3.2.1. Experimental Design

In short: acclimatized Atlantic salmon parr was i.p. vaccinated with half of a full dose of each vaccine. Sterile saline was used as mock vaccine.

The treatment groups were reared in freshwater at 12° C. for 6 weeks whereby intramuscular challenge infection was performed with SPDV. Potency against SPDV was measured as relative percentage protection (RPP) of the vaccinated group compared to the control group, by means of detection of infection with SPDV via PCR of serum.

3.2.2. Test Vaccines

Vaccines used were the same as described in Example 1: Hepta-P and Hepta-C. The control group received sterile Saline (0.9% NaCl). The vaccine given was a half dose: 0.05 ml, delivered intraperitoneally by injection.

3.2.3. Test Animals:

Atlantic salmon, 38 per group, strain: Salmobreed, of mixed sex, and mean weight at vaccination was 28 grams (n=20). The different groups were kept in the same tank, separated by different markings.

3.2.4. Challenge Infection

SPDV challenge was performed at 6 weeks after vaccination. Prior to challenge, all fish were transferred to a challenge facility and kept in one tank for the remaining 10 days of the experiment.

Challenge material was SPDV SAV3 strain PD03-13p2, at 4.75 Log 10 TCID50/ml. Challenge was administered to individual fish by intramuscular injection of 0.05 ml, at the lateral line anterior to the dorsal fin.

3.2.5. Post Challenge Blood Sampling

Ten days post SPDV challenge, individual blood samples for PCR testing were collected from the caudal vein of anesthetized fish. After o/n clotting serum was collected and kept frozen until use.

3.2.6. SPDV Real Time PCR

RNA was extracted from individual sera, that had been spiked with inactivated Equine Influenza Virus, EIV. 35 samples per group were analysed with the SPDV gene nsP1, in a real-time PCR assay, to detect SPDV viremia prevalence as measure of protection against challenge. A real time PCR assay specific for EIV HA gene was also performed to detect the EIV spike added to the serum, as a positive control on the quality of the RNA extraction.

Relative (test vs control) prevalence of SPDV infection (by PCR detection of SPDV in sera) were used to calculate the potency of the tested vaccines, by the prevalence of fish positive for SPDV after challenge. The level of protection was expressed as absolute (+ or –) and as the relative difference in infection prevalence between vaccinated groups and the control group, as a: relative percentage protection (RPP), which is calculated as follows: RPP= [1–(% PCR positive fish in vaccinated group/% PCR positive fish in control group)]×100.

Statistical analysis of the proportion of infected fish in the groups with PCR detected SPDV in serum was performed by the Fisher's exact test, comparing the vaccinated groups to the saline group. In addition the prevalence of positive fish in groups receiving the same dose was also compared pairwise to each other using the Fisher exact test. The level of significance (a) was set to 0.05, and the test was two-sided. Statistical calculations were executed using the SAS program.

3.3. Results and Discussion

All samples were PCR positive for the EIV spike gene, serving as internal control for RNA purification. Therefore all samples were valid for analysis.

An overview of the SPDV PCR results on sera sampled at 10 d post challenge is presented in Table 3, indicating the prevalence and calculated RPP for each group, versus prevalence in the saline group.

TABLE 3

Prevalence and RPP values based on PCR detection
of SPDV in serum at 10 d. p.c.

| Group | % positive (Ct ≤ 35) | RPP % |
|---|---|---|
| Hepta-P (Tween + Span) | 11 | 88 |
| Hepta-C (Cithrol) | 29 | 71 |
| Saline | 97 | 0 |

The PCR results for the saline group showed that the SPDV i.m. challenge was successful since the number of positive fish in this group was 97% (34 out of 35).

The prevalence of SPDV positive fish in all vaccinated groups was significantly lower than that in the control group, as demonstrated by a p value in Fisher's exact test of 0.0001.

Importantly, even though all vaccinated animals only received a half dose of vaccine, the two groups (Hepta-P and Hepta-C) were not significantly different from each other in the prevalence of SPDV infection after challenge; the p value in the two sided Fisher test was 0.133.

3.4. Conclusion

The results show that Cithrol based vaccine formulations protect fish effectively against a challenge infection with SPDV, and to a level of protection (from a half dose) that was not significantly less than that of current commercial vaccines.

4. Example 4: Optimisation of Vaccine Composition 4.1. Introduction

After the new vaccine formulation using a polymeric emulsifier according to the invention was demonstrated to be useful as a safe and efficacious vaccine for fish, other aspects could be optimised. Specifically the viscosity of the new formulation, such as tested in the Hepta-C vaccine described in the above examples, was rather low. Although this clearly did not affect safety or efficacy, it was observed that the new vaccine showed so-called 'sedimentation' upon storage. This means that upon storage, the dispersed aqueous phase tended to move downwards under gravity. This is not the same as breaking of the emulsion, i.e. losing dispersion and showing phase separation. Also, other than breaking, sedimentation is fully reversible, and the phases can be rapidly redistributed by simple shaking by hand prior to administration.

Some level of sedimentation is common for water-in-oil emulsion vaccines, and most product leaflets will recommend a brief shaking of the emulsions before administration. Nevertheless such sedimentation could make a commercial product less attractive visually. Therefore the inventors developed some variants of the formulations tested, to optimise also this aspect of the new emulsion and vaccine.

4.2. Variations Tested

The formulation of the Hepta-C vaccine as tested had a water to oil ratio of 45:55% w/w, and comprised 0.5% w/w Cithrol DPHS; both percentages are expressed by weight of the vaccine. This resulted in a formulation with a viscosity of about 70 mPa·s. The viscosity was measured as described herein.

To prevent, or at least to considerably reduce sedimentation of the aqueous phase, both the water content and the Cithrol content were varied to increase viscosity. Variations tested were: water:oil ratios of 50:50, 60:40, and 70:30% w/w. Also, Cithrol content was increased to 1.0% w/w for some of the samples. The composition of the vaccine-variants tested was essentially the same as that of Hepta-C, apart from the test variables.

To assess the effect of the different compositions on sedimentation, the different vaccine compositions were filled into 500 ml bottles, all to the same volume, and these were stored static for 24 hrs at 4° C. After this period the vertical height of a sedimentation line (if visible) was measured in millimetres, and this was divided by the vertical height of the total volume. Any result of this height ratio below 1 indicated that some level of sedimentation had occurred.

In a smal experiment, similar to the setup in Example 1, the variants of the emulsion vaccines were also tested for their capacity to induce protective levels of antibodies against A. salmonicida, and M. viscosa. Table 5 shows the results of the ELISA titrations; protective Ab titres are levels above 10.7 or 5.8 Log 2 respectively.

4.3. Results

Combined results of viscosity and sedimentation are presented in Table 4. Serology results are presented in Table 5.

TABLE 4

Effect of variations in composition, on viscosity of
water-in-oil formulations with Cithrol as emulsifier

| water:oil ratio (% w/w) | % w/w Cithrol | viscosity (mPa · s) | Sedimentation height ratio |
|---|---|---|---|
| 45:55 | 0.5 | 57.5 | 0.67 |
| 50:50 |  | 72.0 | 0.79 |
| 60:40 |  | 135 | 0.89 |
| 70:30 |  | 265 | 1 |
| 50:50 | 1.0 | 84.0 | 0.83 |
| 60:40 |  | 154 | 0.98 |
| 70:30 |  | 341 | 1 |

TABLE 5

Log2 ELISA titres induced by vaccination with
the variants of the emulsion vaccines

| Vaccine composition | A. salmonicida | M. viscosa |
|---|---|---|
| Saline | ≤6.6 | ≤4.6 |
| Hepta-P | 14.0 | 9.1 |
| Hepta-C, 0.5%, 45:55 | 16.0 | 12.8 |
| Hepta-C, 0.5%, 60:40 | 14.7 | 11.5 |
| Hepta-C, 0.5%, 70:30 | 16.1 | 12.5 |
| Hepta-C, 1%, 50:50 | 15.4 | 12.2 |
| Hepta-C, 1%, 60:40 | 15.9 | 12.3 |
| Hepta-C, 1%, 70:30 | 15.8 | 11.4 |

4.4. Conclusions

Several observations could be made:
- the increase in water content in the emulsion had more effect on viscosity than the increase of Cithrol content
- (almost) complete prevention of sedimentation (after 24 hrs at 4° C.) could be achieved by increasing the water content in the emulsion to a 70:30 water:oil ratio, and/or by increasing the Cithrol content to 1% w/w.
- all vaccine compositions induced protective levels of antibodies against A. salmonicida and M. viscosa.

5. Example 5: Stability Assays of Vaccine Samples

The vaccines Hepta-P and Hepta-C as tested in Example 2 above were subjected to stability assays: an 'in use' stability assay by incubation as 25° C.; where this incubation continued after 8 hours it represents an enhanced stability assay.

At 25° C., Hepta-P vaccine emulsions broke after 5 days, while Hepta-C emulsions remained intact up to the end of the stability experiment at 8 days.

LEGEND TO THE FIGURES

FIG. 1:

Overlay chromatographs comparing the peak patterns of the fatty acids from specific samples:

Panel A: standard sample of oleic acid (2 mg/ml) [solid line], and sample of the prior art emulsifiers [dotted line].

Panel B: samples of test emulsion vaccine 1 (complete heptavalent vaccine) [solid line], and test emulsion vaccine 4 (vaccine without antigens of *M. viscosa* and of *A. salmonicida*) [dotted line]. Horizontal axis: time (minutes); vertical axis: refractive index (nRI).

FIG. 2:

Results of the detection by size exclusion chromatography, of the generation of free fatty acids resulting from the degradation of emulsifiers in prior art emulsion vaccines.

The horizontal axis indicates time in months, of storage at 4° C.; the vertical axis indicates the amount of free fatty acid (FA) measured.

The invention claimed is:

1. A vaccine for the protection of a human or animal target against infection or disease caused by a bacterium, comprising an emulsion, the emulsion comprising an oil phase, an aqueous phase, an emulsifier and non-live bacterial antigen,
    wherein the emulsifier is a polymeric emulsifier which is a block copolymer having a general formula A-B-A in which component B is the divalent residue of a water-soluble polyalkylene glycol and component A is the residue of an oil-soluble complex monocarboxylic acid, and
    wherein the non-live bacterial antigen comprises a bacterial esterase.

2. The vaccine of claim 1, wherein the vaccine is for the protection of an animal target.

3. A method of vaccinating a human or animal target against infection or disease caused by a bacterium, comprising administering to said target the vaccine of claim 1.

4. A method of vaccinating an animal target against infection or disease caused by a bacterium, comprising administering the vaccine of claim 2 to said animal target.

5. The vaccine of claim 2, wherein the animal target is a fish.

6. A method of vaccinating a fish against infection or disease caused by a bacterium, comprising administering the vaccine of claim 5 to said fish.

7. The vaccine of claim 1, wherein component A is a polyhydroxystearic acid, and component B is a polyethylene glycol.

8. The vaccine of claim 1, wherein the polymeric emulsifier is a PEG-30-di-(polyhydroxystearate).

9. The vaccine of claim 1, wherein the non-live bacterial antigen comprises an inactivated whole bacterial culture, or part of an inactivated bacterial culture.

10. The vaccine of claim 9, wherein the part of an inactivated bacterial culture is selected from any of: a pellet, supernatant, concentrate, dialysate, extract, sonicate, lysate or fraction of a culture inactivated bacterial culture.

11. The vaccine of claim 9, wherein the non-live bacterial antigen is selected from the group consisting of: an inactivated bacterial cell, an intact inactivated bacterial cell or a damaged inactivated bacterial cell.

12. The vaccine of claim 1, wherein the non-live bacterial antigen comprises a *Aeromonas salmonicida* and/or *Moritella viscosa* non-live bacterial antigen.

* * * * *